United States Patent [19]

Aston et al.

[11] Patent Number: 5,534,492

[45] Date of Patent: Jul. 9, 1996

[54] MURAMYL PEPTIDE FOR THE TREATMENT OF TOXICITY

[75] Inventors: Roger Aston, Wiltshire, United Kingdom; Igor E. Kovalev, Moscow, U.S.S.R.

[73] Assignee: Peptech (UK) Limited, London, United Kingdom

[21] Appl. No.: 302,692

[22] PCT Filed: Feb. 26, 1993

[86] PCT No.: PCT/GB93/00408

§ 371 Date: Jan. 3, 1995

§ 102(e) Date: Jan. 3, 1995

[87] PCT Pub. No.: WO93/16713

PCT Pub. Date: Sep. 2, 1993

[30] Foreign Application Priority Data

Feb. 28, 1992 [GB] United Kingdom ............... 9204354

[51] Int. Cl.⁶ .................................................. A61K 37/02
[52] U.S. Cl. ........................... 514/8; 514/17; 514/18; 514/19; 514/810; 514/811; 514/812; 514/813; 260/998.2
[58] Field of Search .................. 514/2, 8, 17, 18, 514/19, 810, 811, 812, 813; 260/998.2

[56] References Cited

PUBLICATIONS

Farghali et al "Muramyl Dipeptide and Carbon Tetrachloride Hepatotoxicity in Rats! Involvement of Plasma Membrane and Calcium Homeostasis in Protective Effect" Meth and Find Exptl Clin Pharmacology 1986; 8(8):469–477.

Farghali et al "The Protection from Hepatotoxicity of Some Compounds by the Synthetic Immunomodulator Muramyl Dipeptide (MDP) in Rat Hepatocytes and In Vivo" Meth and Find Exptl Clin Pharmacol. 1984; 6(8):449–454.

*Primary Examiner*—Nathan M. Nutter
*Attorney, Agent, or Firm*—Banner & Allegretti

[57] ABSTRACT

Muramyl peptide compounds are useful in the treatment of toxicity, particularly when this condition results from alcohol, hypnotics or sedatives, anaesthetics, opioids or drug abuse generally. The muramyl peptide compound may be of either of general formulae I and II:

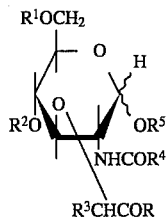

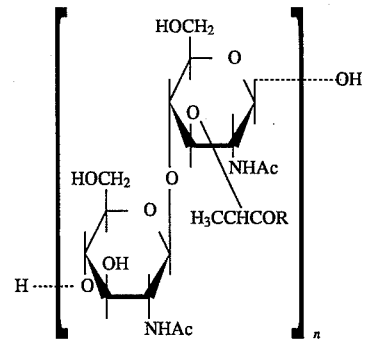

Preferred compounds include prototype MDP, muroctasin, MTP-PE, murabutide, t-MDP, N-acetyl-glucosaminyl-N-acetyl-muramyl-L-alanyl-D-isoglutamine (GMDP) and N-acetyl-glucosaminyl-N-acetyl-muramyl-L-alanyl-D-glutamic acid (GMDP-A).

23 Claims, 5 Drawing Sheets

MURAMYL PEPTIDE FOR THE TREATMENT OF TOXICITY

This invention relates to the treatment, prophylaxis and management of toxicity caused by a variety of toxic substances, including alcohol, anaesthetics and narcotics.

Human and other animal bodies have developed a number of approaches to detoxifying toxic substances. The range of toxic substances likely to be encountered is extremely broad, particularly for humans but also for animals, and so it would be impracticable for the organism to have enzymes in store to deal specifically with all the new compounds already produced and yet to be produced by the organic chemist; such enzymes as are already available must serve as effectively as possible.

In some ways any study of detoxification is hampered by the difficulty of deciding precisely what constitutes a toxic substance. Many compounds develop toxicity if the dose is sufficiently great and some species are quite resistant to substances which are extremely toxic in others. Also the time of exposure to the toxic substance is important, as is the route by which it enters the body. However, in spite of this diversity both in the nature of the compounds likely to be encountered and in the different effects which can be exhibited by a single compound, there is in practice little difficulty in determining whether a compound is toxic and needs to be detoxified by the body. Possibly related to this, there is a remarkably small number of types of reaction which the human or animal body uses to deal with many toxic substances: the most commonly encountered are hydroxylation, oxidation, reduction and conjugation. Many of these reactions take place in the liver.

A wide variety of compounds are detoxified by hydroxylation, frequently mediated by the cytochrome $P_{450}$ system, which uses $NADPH+H^+$ as a reductant; molecular oxygen is also required and the substance is hydroxylated in the process. This system appears to interact with many different chemical types of compounds, including aliphatic, aromatic and unsaturated compounds and those containing sulphur and nitrogen. Common drugs hydroxylated include: (a) barbiturates such as phenobarbitone (a sedative); (b) antipyrine (an analgesic and antipyretic); (c) amphetamine (a stimulant); (d) heroin (a narcotic); (e) meprobromate (a tranquilliser); and (f) acetanilide. Many toxic substances themselves stimulate the activity of hydroxylating systems in vivo. The consequence of hydroxylation is an easier elimination of unwanted foreign substances because of their conversion from lipid-soluble molecules into more polar substances.

Reduction is another method of detoxication and is a reaction used to detoxify aromatic nitro groups, for example. Nitrobenzene is reduced (and hydroxylated) to p-aminophenol.

Conjugation is one of the most versatile methods of detoxication. Glycine is frequently the conjugating substance. It reacts with carboxyl groups of organic acids to form a substituted amide: for example, hippuric acid is formed as a conjugate of benzoic acid and glycine. In fact, this conjugation proceeds through a benzoyl-CoA intermediate, which serves as another example of the role of coenzyme A in detoxication by conjugation. Other conjugations involve formation of sulphate esters (as in the metabolism of phenol and unwanted steroid hormones) and acetylated or methylated derivatives. Glucuronic acid is also involved in conjugate formation.

Oxidation is another way of metabolising unwanted material. Often the products are organic acids. For example, benzylamine is converted to benzoic acid by oxidation of the amino group, presumably by an amine oxidase and aldehyde dehydrogenase. The toxic effect of alcohol (that is to say, ethyl alcohol or ethanol) is mediated by its oxidised metabolite acetaldehyde (Cedarbaum and Rubin *Federation Proc.* 34 2045 (1975)). Ethanol is oxidised to acetaldehyde by the enzyme alcohol dehydrogenase (EC 1.1.1.1). Ethanol also has the effect of inducing the cytochrome $P_{450}$ system. In the absence of the induction of the metabolism of acetaldehyde (for example by oxidation by aldehyde dehydrogenase to acetic acid, which is in turn conjugated by the action of acetyl thiokinase to form acetyl-CoA), the level of acetaldehyde will rise with destructive effects (Takeuchi and Takeda *Alcohol and its Hepatic Effects*, In: "Alcohol Liver Pathology", Khanna et al., Eds., Addiction Research Foundation of Ontario, Toronto, 1975). Acetaldehyde gives rise to nausea, hypotension and vomiting, and also stimulates collagen synthesis: drugs which block this effect have a beneficial influence on alcoholic cirrhosis in vivo (Lieber *Pathogenesis of Alcoholic Liver Disease* in "Internat. Symp. on Drugs and the Liver", Fundazione Giovanni Lorenzini, Milan, 1991, p64).

From the above, it can be seen that there is a considerable degree of overlap between the common metabolic detoxifying reactions. This may be a reason why it appears to be possible to assist or promote detoxification of a considerable number of toxic substances by the administration of certain compounds: it is to this that the present invention is addressed. It has been discovered that a group of compounds, some of which have previously been disclosed as having immunopotentiating, anti-tumour and certain antibacterial activities, is useful in preventing, treating or managing toxicity.

According to the present invention, there is provided the use of a muramyl peptide compound in the manufacture of a medicament for the treatment, prevention or management of toxicity.

It has long been known that non-specific stimulation of the immune system can be brought about by exposure to bacteria, or components extracted from bacterial cells. The specific components responsible for this activity were identified as sugar-containing peptides of the cell wall, and further biochemical analysis of the peptides identified them as the peptidoglycan component of the cell wall. The smallest effective synthetic molecule was found to be an N-acetylmuramyl-L-alanyl-D-isoglutamine (Merser et al, *Biochem. Biophys. Res. Comm.* 66 1316 (1975)). The ability of this compound (now frequently referred to as "prototype muramyl dipeptide" or "prototype MDP") to protect mice against bacterial infection (*Klebsiella pneumonia*) has been described (Chedid et al, *Proc. Natl. Acad. Sci. USA*, 74 2089 (1977)).

Subsequently, a wide variety of analogues of prototype muramyl dipeptide were synthesised, some of which have been proposed as treatments for the restoration of immune function or the non-specific stimulation of the immune system. These analogues, and prototype MDP itself, are muramyl peptide compounds.

The expression "a muramyl peptide compound" has a clear meaning to those skilled in the art. In particular, it refers to a compound containing one or more sugar residues, at least one of the sugar residues, which will often be a muramic acid residue, being substituted with at least one or more (and usually two or more) amino acid residues. Muramyl peptide compounds may be peptidoglycans which are capable of enhancing the cellular antigenicity response in mammals and being prototype MDP or analogues or derivatives thereof. Many muramyl peptide compounds, as the term is used in this specification, fall within general formula I:

wherein:

$R^1$ represents a hydrogen atom or a $C_1$–$C_{22}$ acyl group;

$R^2$ represents a hydrogen atom or a $C_1$–$C_{22}$ acyl group;

$R^3$ represents a hydrogen atom or a $C_1$–$C_6$ alkyl group;

$R^4$ represents a $C_1$–$C_{21}$ alkyl group or a $C_6$ or $C_{10}$ aryl group;

$R^5$ represents a hydrogen atom; and

R represents the residue of an amino acid or a linear peptide built up of from 2 to 6 amino acid residues, at least one of the residues being optionally substituted with a lipophilic group.

Preferred acyl groups for $R^1$ and $R^2$ are $C_1$–$C_5$ acyl groups such as acetyl; it will be appreciated that the carbon count in the acyl group does not include the carbonyl moiety. Preferred alkyl groups for $R^3$ are $C_1$–$C_4$ alkyl groups such as methyl and ethyl. Preferred alkyl groups for $R^4$ and $C_1$–$C_6$ alkyl groups, particularly $C_1$–$C_4$ alkyl groups, such as methyl or ethyl; phenyl is a preferred aryl group.

R preferably represents a mono-, di- or tri-peptide. The proximal peptide residue (or the only peptide residue, if there is only one) is preferably that of an L-amino acid. Examples include:

L-alanyl
L-valyl
L-leucyl
L-isoleucyl
L-α-aminobutyryl
L-seryl
L-threonyl
L-methionyl
L-cysteinyl
L-phenylalanyl
L-tyrosyl
L-tryptophanyl
L-lysyl
L-ornithyl
L-arginyl
L-histidyl
L-glutamyl
L-glutaminyl
L-aspartyl
L-asparaginyl
L-prolyl
L-hydroxyprolyl L-alanyl is preferred, as is L-threonyl.

The next amino acid from the proximal end of the peptide is preferably of the D-configuration. It is preferably acidic and may be D-glutamic or D-aspartic acid or a mono-, di- or mixed $C_1$–$C_{22}$ (preferably $C_1$–$C_6$) alkyl ester, amide or $C_1$–$C_4$ alkyl amide thereof. (The expression "mixed" is illustrated when one carboxyl group is amidated and the other esterified. D-isoglutamine and D-glutamate are preferred.

A third amino acid residue from the proximal end of the chain, if there is one, is preferably of the L-configuration, as indicated above in relation to the proximal amino acid residue. L-alanyl and L-lysyl are preferred.

The amino acid residue or linear peptide is optionally substituted with at least one lipophilic group. The lipophilic group may be a $C_{10}$–$C_{22}$ acyl group such as stearoyl or a di-($C_{10}$–$C_{22}$ acyl)-sn-glycero-3'-hydroxyphospheryloxy-group wherein for example each of the $C_{10}$–$C_{22}$ acyl groups can be a palmitoyl group. The lipophilic group may alternatively (or in addition, as more than one substitution may be present) be a $C_1$–$C_{10}$ ester group, such as a $C_2$–$C_6$ ester group: a butyl ester is an example.

Examples of muramyl dipeptides within the scope of general formula I include:

prototype muramyl dipeptide (N-acetylmuramyl-L-alanyl-d-isoglutamine);

muroctasin, otherwise known as MDP-Lys (L18) ($N^2$-(N-acetylmuramyl-L-alanyl-D-isoglutaminyl)-$N^6$-stearoyl-L-lysine);

MTP-PE (N-acetyl-muramyl-L-alanyl-D-isoglutaminyl-L-alanyl-2-(1',2'-dipalmitoyl-sn-glycero-3 '-hydroxyphosphoryloxy)ethylamide, monosodium);

murabutide (N-acetylmuramyl-L-alanyl-D-glutamine-α-N-butyl ester); and t-MDP (N-acetylmuramyl-L-threonyl-D-isoglutamine).

The preparation of muramyl dipeptide is disclosed in DE-A-2450355 and U.S. Pat. No. 4,235,771. The preparation of muroctasin is disclosed in EP-A-0021367 and U.S. Pat. No. 4,317,771. The preparation of MTP-PE is disclosed in EP-A-0025495. The preparation of murabutide is described in Lefrancier et al., *J. Med. Chem.*, 25 87 (1982). The preparation of t-MDP can be prepared by methods known in the art. Patent publications which give details of the preparations of muramyl peptide compounds generally include BE-A-0834753, BE-A-0834754, BE-A-0847103, BE-A-0849214, DE-A-2710455, DE-A-2922533, DE-A-2747379, DE-A-2912865, FR-A-2355505, FR-A-2358159, FR-A-2375249, EP-A-0004512, EP-A-0002677, JP-A-54063016, JP-A-54073729, JP-A-55019236, U.S. Pat. No. 4,082,735 and U.S. Pat. No. 4,082,736. All the documents referred to in this specification are incorporated herein by reference.

Not all muramyl dipeptides useful in the present invention fall within general formula I. Many fall within general formula II, which represents a very much preferred group of compounds for use in the invention:

wherein:

R represents a residue of an amino acid or a linear peptide built of from 2 to 6 amino acid residues, at least one of the residues being optionally substituted with a lipophilic group; and n is 1 or 2.

Preferred values for R are as described above in relation to general formula I. It is particularly preferred that the peptide R correspond to the peptide in prototype MDP (L-Ala-D-isoGln). Alternatively, in another preferred embodiment, R may represent L-Ala-D-Glu.

The preferred value for n is 1.

Compounds of general formula II are disclosed in U.S. Pat. No. 4,395,399 and the preferences set out in that document are equally preferred in the present invention. Additionally, in this invention, the group R may be substituted lipophilically as described above.

One of the most preferred compounds for use in the present invention falls within general formula II and is N-acetyl-glucosaminyl-N-acetyl-muramyl-L-alanyl-D-isoglutamine (GMDP), the structure of which is:

GMDP

This compound (Compound II in U.S. Pat. No. 4,395,399), also known as glycopin, has already undergone preclinical toxicity testing and pharmacokinetic investigations required for licensing for clinical use in the USSR. The acute toxicity in mice, measured by the $LD_{50}$ test is 7 g/kg. This figure shows the compound to be almost an order of magnitude less toxic than muroctasin which has an $LD_{50}$ value in mice of 625 mg/kg.

GMDP also has the particular advantage, shared with the other glucosaminyl-muramyl peptides of U.S. Pat. No. 4,395,399, of being water soluble: this is a real benefit for parenteral administration. The choice of this muramyl dipeptide which in many ways is contrary to the trend in the art. Both muroctasin and MTP-PE have been specifically synthesised to incorporate a lipophilic group, and many non-lipophile-substituted muramyl dipeptides have been formulated in lipophilic preparations such as liposomes (as in U.S. Pat. No. 4,522,811 and U.S. Pat. No. 4,684,625), purportedly to enhance the activity of the muramyl dipeptide. In the present invention, water solubility is preferred.

GMDP has a further advantage, as do other muramyl dipeptides within the scope of general formula II at least, of being readily formulatable for oral administration. This is always the preferred route of administration of a pharmaceutically active compound, and so represents a route of administration of choice for MDPs. Intranasal administration may be preferred in certain circumstances, and parenteral administration, such as by the subcutaneous, intra-muscular or intravenous routes, is not ruled out.

Pyrogenicity is a problem which has caused difficulties for the exploitation of certain muramyl dipeptides. Pyrogenicity may be attenuated by appropriate formulations (see, for example, the liposomal formulations of U.S. Pat. Nos. 4,522,811 and 4,684,625), but in general it will be preferable to choose, for use in the present invention, a muramyl dipeptide which has low intrinsic pyrogenicity. While the pyrogenicity of GMDP is sufficiently low not to have prevented its clinical evaluation, it may in some circumstances be preferable to use a substantially non-pyrogenic analogue. Such an analogue is available, and is N-acetyl-glucosaminyl-N-acetyl-muramyl-L-alanyl-D-glutamic acid (GMDP-A), which is Compound III in U.S. Pat. No. 4,395,399, and whose structure is as follows:

GMDP-A

Glucosaminyl-muramyl dipeptides within the scope of general formula II can be prepared relatively cheaply and in reasonable large quantities by the process disclosed in U.S. Pat. No. 4,395,399. The preparation disclosed is based on the extraction and purification of the disaccharide component from the bacterium *Micrococcus lysodecticus* and its subsequent chemical linkage to a dipeptide synthesised for example by conventional peptide chemistry.

Compounds of general formula II are proposed for use in the treatment or prevention of septic shock in UK Patent Application No. 9124500.1, filed 19 Nov. 1991.

As stated above, by means of the present invention, muramyl dipeptides are useful in the prevention, treatment or management of toxicity. Toxic substances may be ingested or generated in vivo. In particular, the invention has application in alcohol detoxification, anaesthetic recovery and in recovery or withdrawal from hypnotics, narcotics, sedatives or other drugs, especially in the case of abuse. Recovery from narcosis and treatment of withdrawal (so as to mitigate or avoid one or more usual withdrawal symptoms) are particular areas in which the invention has applicability. The exact mechanism by which the compounds useful in the invention exhibit their beneficial effect is not known with precision. Possibly there is a connection with the observation previously made that GMDP at least stimulates the synthesis of the superoxide anion ($O_2^-$) in the cells of the reticulo-endothelial system (Balitsky et al., *Int. J. Immunopharmacol.* 11(5) 429–434 (1989)); this in turn could activate aldehyde dehydrogenase and/or other enzymes. For the moment, though, the reason for the observed efficacy must remain a matter for speculation.

The invention may have application in the prevention, treatment or management of toxicity caused directly or indirectly by one or more of the following compounds or groups of compounds (and, where appropriate, salts, hydrates and derivatives of them):

(a) ethanol and its metabolites (principally acetaldehyde);

(b) hypnotics and sedatives, including: benzodiazepines (such as alprazolam, chlordiazepoxide, clonazepam, chlorazepate, demoxepam, diazepam, flurazepam, halazepam, lorazepam, midazolam, nitrazepam, nordazepam, oxazepam, prazepam, temazepam, triazolam and Ro 15-1788); barbiturates (such as amobarbital, aprobarbital, butabarbital, butalbital, mephobarbital, metharbital, methohexital, pentobarbital, hexobarbital, phenobarbital, secobarbital, talbutal, thiamylal and thiopental); chloral derivatives (such as chloral, hemiacetals of chloral and triclofos); ethchlorvynol; glutethimide; methyprylon; meprobamate; methaqualone; paraldehyde; ethinamate; etomidate; and clomethiazole;

(c) anaesthetics, including: inhalational anaesthetics (such as methoxyflurane, halothane, enflurane, isoflurane and nitrous oxide); intravenous anaesthetics (such as barbiturates (see above), benzodiazepines (see above), etomidate, opioid analgesics and neuroleptic-opioid combinations); and local anaesthetics (such as cocaine, procaine, chloroprocaine, lidocaine, tetracaine, mepivacaine, bupivacaine and etidocaine; and (d) opioids, including: morphine and related opioids (such as morphine itself, heroin, hydromorphone, oxymorphone, levorphanol, levallorphan, codeine, hydrocodone, oxycodone, nalorphine, naloxone, naltrexone, buprenorphine, butorphanol and nalbuphine); meperidine and congeners (such as mepiridine itself, alphaprodine, diphenoxylate and fentanyl) and methadone and congeners (such as methadone itself and propoxyphene); and (e) other drugs subject to abuse, including: CNS sympathomimetics (such as amphetamines [particularly amphetamine, 2,5-dimethoxy-4-methylamphetamine, dimethoxyamphetamine 3,4-methylenedioxyamphetamine 5-methoxy-3,4-methylenedioxyamphetamine and p-methoxyamphetamine], cocaine and related drugs); nicotine and tobacco; cannabinoids (such as 1-$\Delta^9$-tetrahydrocannabinol and 1-$\Delta^8$-tetrahydrocannabinol); and psychedelic drugs, which are often hallucinogenics and/or psychotomimetics and/or psychotogenics, (such as lysergic acid diethylamide (LSD), dimethyltryptamine (DMT), psilocin, mescaline and arylcyclohexamines including phencyclidine).

MDPs and, in particular, GMDP, may induce oxidation of all these substances since it has been established that they have the ability to enhance the cytochrome $P_{450}$ system.

Precisely how the toxicity of the compound manifests itself will of course depend on the nature of the compound. Narcosis is one manifestation of toxicity. Many toxic compounds can cause brain damage and, ultimately, death. Indirect toxic effects may be seen on withdrawal from use of a drug, and so the invention is also useful in aiding the withdrawal process.

The invention has application in dealing with endogenously created substances. Acetaldehyde, the primary metabolite of ethanol, is a case in point.

Additionally, the invention has application when a toxic substance is generated in vivo by other metabolic processes, for example as a result of disease. Jaundice is a case in point. In hepatogenous jaundice, bile acids or their metabolites may be toxic; in haemolytic jaundice, the toxic substances are derived from the breakdown products of red blood cells.

It seems that the muramyl peptides useful in the present invention act by enhancing the activity of various hepatic metabolic processes and therefore in a second aspect of the invention there is provided the use of a muramyl peptide compound in the manufacture of a medicament for enhancing hepatic metabolism of toxins.

As mentioned above, the toxins may be endogenously created substances such as acetaldehyde, bile acids and their metabolites and the breakdown products of red blood cells, particularly bilirubin. Alternatively, the toxin may be an exogenous one such as alcohol or a narcotic substance, for example one of those described above.

Muramyl peptides are useful for treating any patient with reduced liver function, for example, geriatric patients or cancer patients, particularly those with advanced hepatic metastases. In such patients, toxins tend to accumulate in the body leading to a variety of problems. One endogenous toxin which can cause problems is bilirubin. High levels of bilirubin are known to result in jaundice, particularly in babies and patients with reduced liver function. In addition, in cancer patients, levels of drugs such as analgesics and chemotherapeutic agents which are used to treat the patient tend to build up in the body and this can lead to severe side effects.

However, the present inventors have been able to demonstrate that the level of metabolites such as bilirubin in the blood of patients could be significantly reduced when the patients were treated with a muramyl peptide.

Detoxification with muramyl peptides seems to be particularly effective for substances which undergo detoxification by oxidation and this appears to be because muramyl peptides are capable of stimulating the cytochrome $P_{450}$ system.

Therefore, in a third aspect of the present invention, there is provided the use of a muramyl peptide compound in the manufacture of a medicament for enhancing the activity of the cytochrome $P_{450}$ system.

This activity of muramyl peptides is particularly surprising because, as discussed above, muramyl peptides are non-specific immunostimulants. It has long been known that there is a reciprocal relationship between the $P_{450}$ system and the immune system (Nebert et al, *Adv. in Genetics*, 21, 1–52 (1982). Also, the administration of non-specific immunostimulants suppresses $P_{450}$-mediated monooxygenase activity and, conversely, certain monooxygenase inducers have been shown to cause immunosuppression. Examples of non-specific immunostimulants which have been shown to act in this way include stable heat killed suspensions of *Corynebacterium parvum*, BCG vaccine, interferon-stimulating agents and other anti-tumour bacterial preparations (Mannering and Deloria, Ann. Rev. Pharmacol. Toxicol. 26: 455–515 (1980)).

Surprisingly, it has been found that MDPs and, in particular, GMDP, differ from other non-specific stimulants of the immune system since they not only fail to inhibit the hepatic metabolism of chemical toxins in an organism but they can actually enhance the cytochrome $P_{450}$ system. This means that the detoxification mechanism of the patient is enhanced.

Because of this combination of stimulation of the immune system and enhancement of hepatic detoxification mechanisms, muramyl peptides such as GMDP and its analogues are potentially extremely valuable agents for combatting the various physical effects which generally accompany poisoning with alcohol and other toxic substances such as narcotics as well as other disorders associated with liver dysfunction.

Examples of conditions which muramyl peptides may be particularly useful in treating are:

i) alcohol-associated hepatitis and hepatic cirrhosis;

ii) viral hepatitis—the combination of stimulation of the cytochrome $P_{450}$ system and the immune system may be particularly useful in such cases;

iii) liver failures of whatever cause; and iv) hepatic encephalopathy.

It is possible that there may be other reasons for the detoxifying action of muramyl peptides in addition to the mechanisms mentioned above.

From the above, it can be seen that the invention also relates to a method for the prevention, treatment or management of toxicity, the method comprising administering to a patient an effective amount of a muramyl dipeptide. Preferences for this aspect of the invention are as given above.

In addition, the invention relates to a method for enhancing hepatic metabolism of toxins and to a method for enhancing the activity of the cytochrome $P_{450}$ system, both these methods comprising administering to a patient an effective amount of a muramyl dipeptide. Again, preferences for both of these aspects of the invention are as given above.

As briefly discussed previously, muramyl dipeptides may be administered either parenterally or non-parenterally (usually, and preferably, orally). Formulations for parenteral administration will generally be sterile. One or more suitable carriers will be present, such as physiological saline. Muramyl dipeptides may be lyophilised with a protectant compound such as glycine prior to formulating with physiological saline or water for injection.

Oral formulations are preferred, particularly those in the form of tablets. One or more suitable carriers may be present. Typical carriers include lactose, saccharose, potato starch, calcium stearate and methyl cellulose.

The precise dosage for administration will always be that deemed suitable by the clinician or physician. Subject to that, a daily dosage in the range of from 0.1 to 100 mg per day (or per tablet or other unit dose) may be found to be acceptable, with a range of 0.5 mg to 5 mg or 10 mg per day (or per tablet or other unit oral dose) being preferred. A daily dosage of 1.0 mg is considered to be optimal.

Dosages for parenteral (for example, intravenous, intramuscular or subcutaneous) administration will generally be lower, with from 0.01 mg to 1 mg per day (or per unit dose) being suitable. A range of from 0.05 mg to 0.5 mg per day (or per unit dose) is preferred, and a dosage of about 0.1 mg per day is optimal.

The timing of the dosage will also be best determined by the clinician or physician.

BRIEF DESCRIPTION OF THE DRAWINGS

The invention will now be illustrated by the following non-limiting examples. The examples refer to the accompanying drawings, in which.

EXAMPLE 1

Figure 1:
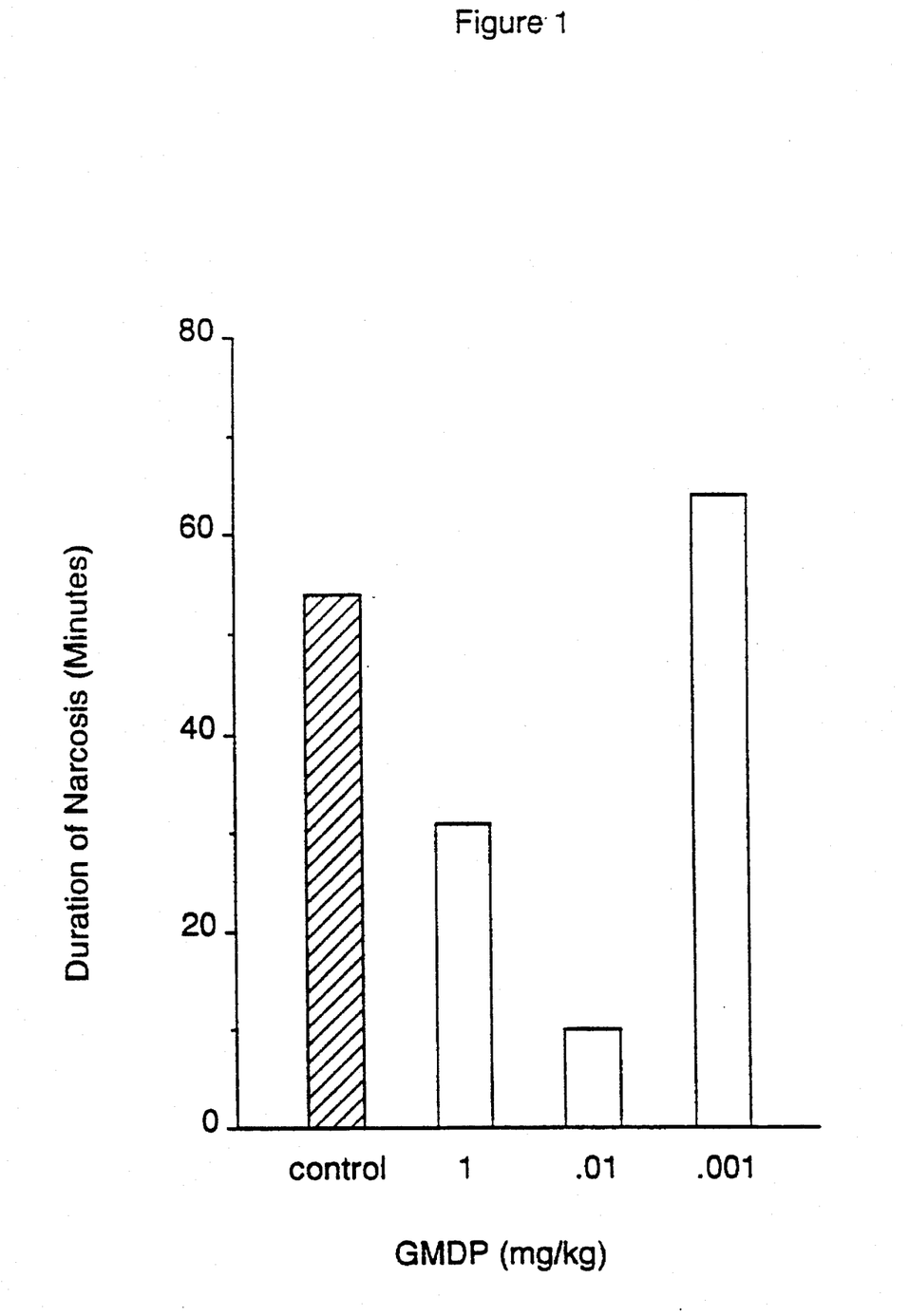
FIG. 1 shows the influence of GMDP on the duration of ethanol narcosis in outbred white mice.

Outbred white mice were given three intraperitoneal injections of GMDP at daily intervals and challenged with ethanol (4.5 g/kg IP) after the last GMDP injection. Narcosis was defined as the time in the lateral position ("leglessness"). FIG. 1 shows the duration of narcosis (in minutes) for the control group and for groups of mice given GMDP at dosages of 1, 0.01 and 0.001 mg/kg. Each group contained 10 to 12 mice. It can be seen that in the control group narcosis lasted for between 50 and 60 minutes, whereas in the groups administered with at least 0.01 mg/kg GMDP, narcosis was of a much shorter duration.

EXAMPLE 2

Figure 2:
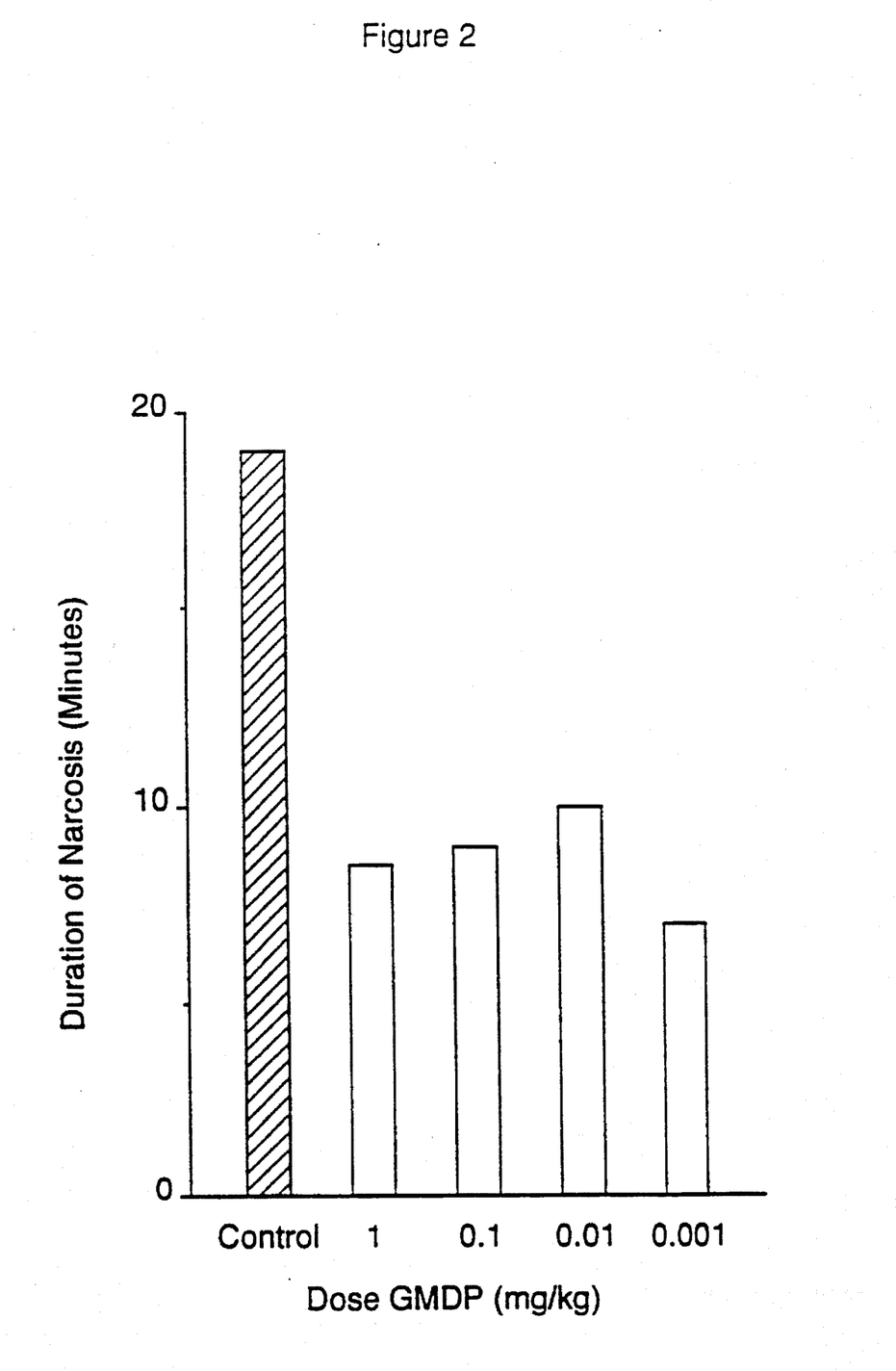
FIG. 2 shows the influence of GMDP on the duration of acetaldehyde narcosis in outbred mice.

The procedure of Example 1 was followed but modified to study the duration of acetaldehyde narcosis. Acetaldehyde, at 450 mg/kg was administered IP after the last GMDP dose, instead of the ethanol. The results are shown in FIG. 2, from which it can be seen that GMDP markedly shortened the duration of narcosis induced by acetaldehyde.

EXAMPLE 3

In this example, the influence of GMDPA and various GMDP or GMDPA analogues on ethanol narcosis was studied. The procedure of Example 1 was followed, except that instead of the GMDP, one of the following compounds was administered IP at 1 mg/kg daily for three days:

GMDPA (GMDPA)$_2$

Stearoyl-GMDP and

Stearoyl-GMDPA

Figure 3:
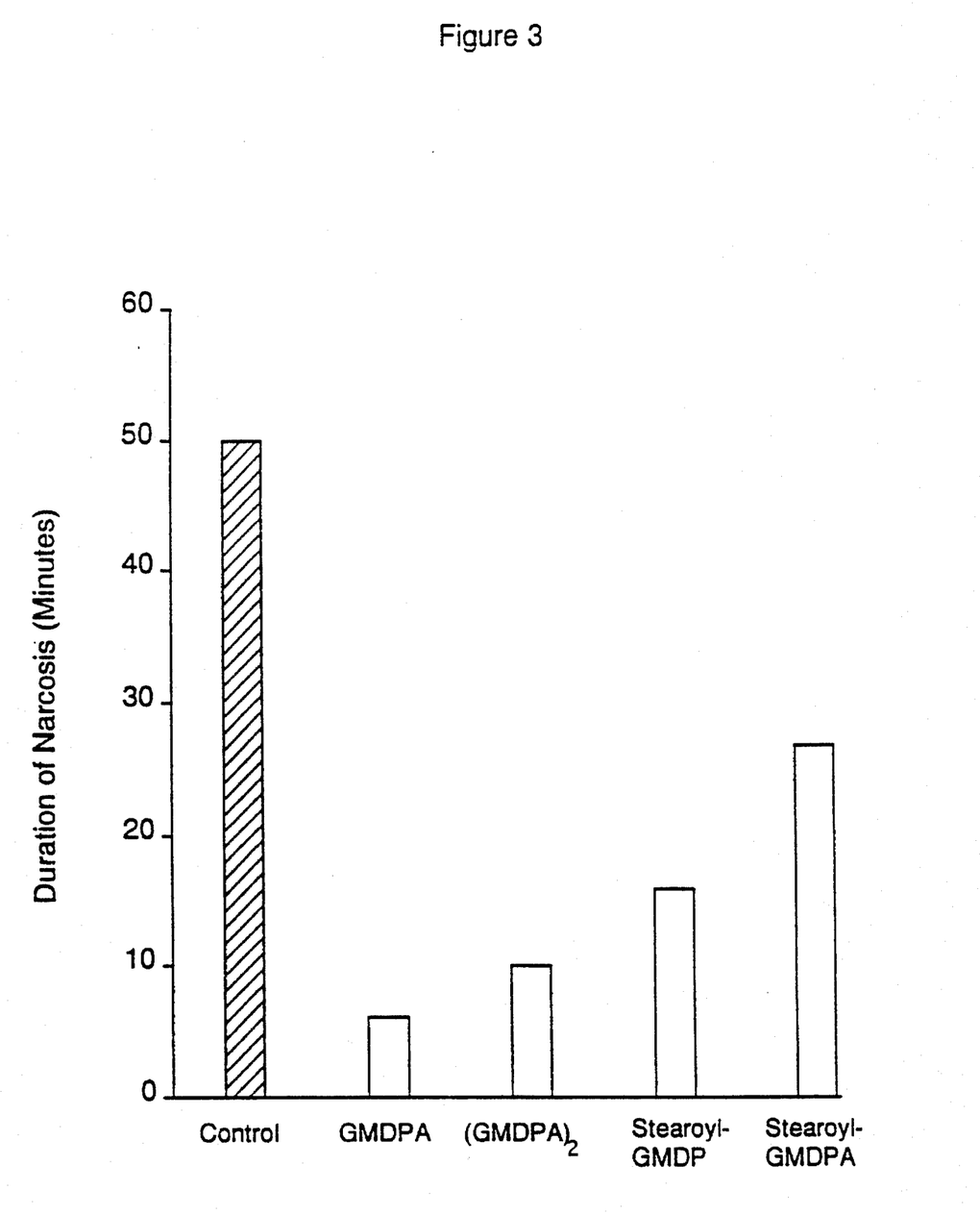
FIG. 3 shows the influence of GMDPA and analogues on ethanol narcosis in white mice.

The results are shown in FIG. 3, from which it can be seen that all the compound markedly reduce the duration of narcosis, compared to the control.

EXAMPLE 4

Figure 4:
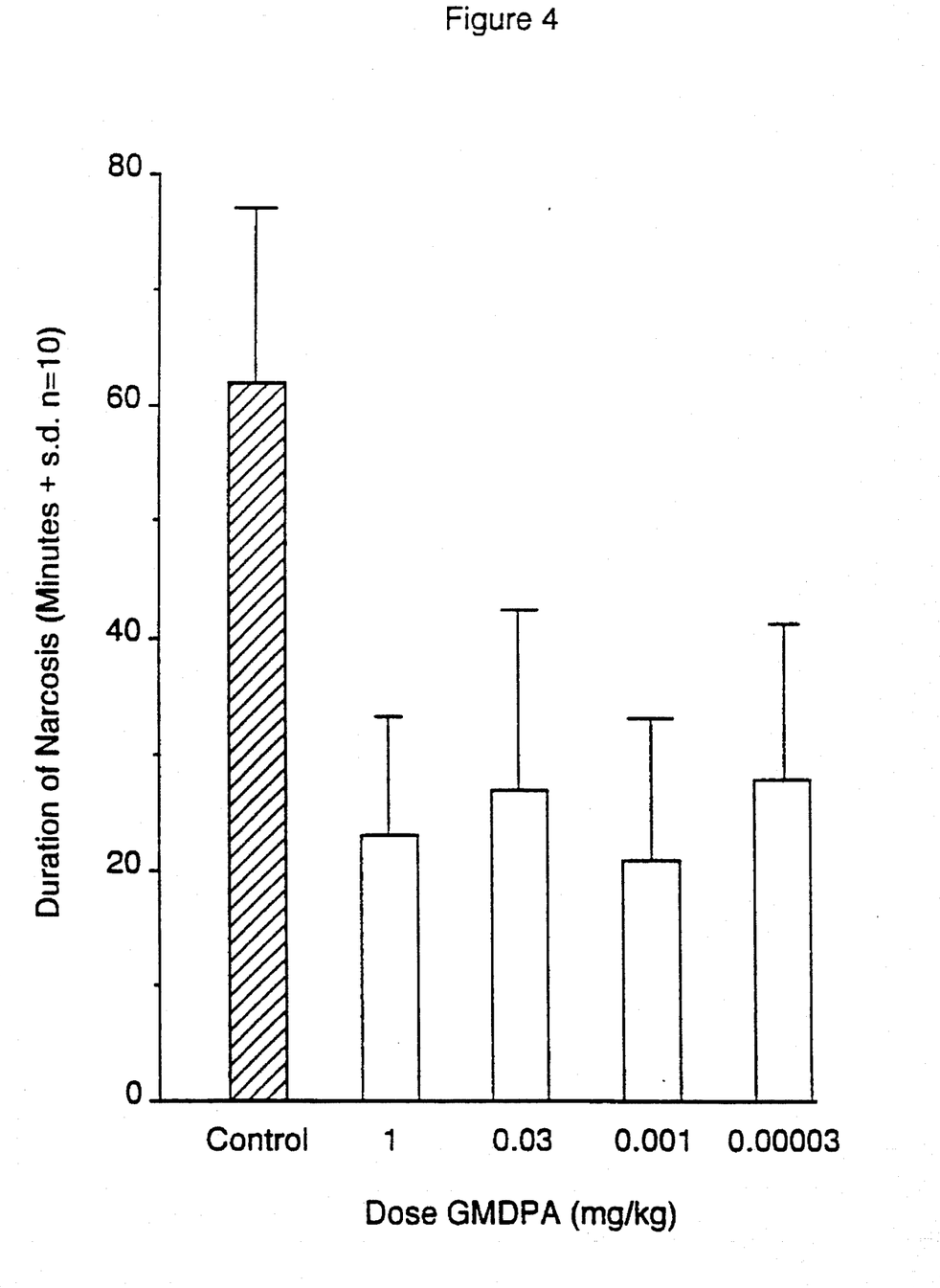
FIG. 4 shows the influence of GMDPA on acetaldehyde narcosis in inbred C57 B1/6 mice.

This example studies the influence of GMDPA on acetaldehyde narcosis in inbred C57 B1/6 mice. The procedure of Example 1 was generally followed except that GMDPA was injected IP daily for three days and acetaldehyde was given 1, 4, 8 or 12 days later. The inhibition of narcosis occurred at 1, 4 and 8 days, but not 12. FIG. 4 shows the results for acetaldehyde administered at day 4.

The results of the experiments described in Examples 1 to 4 demonstrate that the inactivation of ethanol and acetaldehyde is accelerated in the presence of GMDP. Therefore, GMDP and its analogues may be useful as detoxicating means, preventing development of liver pathology (hepatitis, cirrhosis), heart failure and other pathologies in persons who abuse alcohol. The combination of immunostimulating and detoxifying effect of GMDP and its analogues gives a unique possibility to create a fundamentally new type of therapy of illnesses accompanying alcoholism.

It should be stressed that GMDP cannot be a means of emergency first aid in cases of acute alcohol poisoning. It is not a means of fighting against abuse of narcotics but rather a means of therapy of complications caused by alcohol and mainly by its highly reactive metabolite acetaldehyde. The experiments, aimed at the study of GMDP influence on the narcotic effect of ethanol and acetaldehyde, should not be considered as an attempt to relieve actual poisoning. This test is used as pharmacological testing of the rate of ethanol and acetaldehyde metabolism in the organism (mainly in liver). It should be noted that cytochrome $P_{450}$ system plays an important part in ethanol metabolism (oxidation), along with other well-known enzymes.

It is common knowledge that people who suffer from alcoholism and chronically abuse alcohol, have a diminished metabolic cytochrome $P_{450}$-dependent liver function.

EXAMPLE 5

This example studies the effect of GMDP on the duration of narcosis induced by hexobarbital.

GMDP was administered orally to mice 15 minutes before the intraperitoneal injection of hexobarbital (HEXENAL™) at 50 mg/kg. The duration of narcosis (preservation of the lateral position) was recorded. The results are shown in Table 1, below.

TABLE 1

The effect of GMDP on the duration of HEXENAL narcosis in mice

| Dose GMDP mg/kg | Narcosis duration Min (M ± m) | Effect % (M ± m) |
|---|---|---|
| — | 60.48 ± 7.12 | 0 ± 11.77 |
| 0.01 | 15.48 ± 4.93* | −74.01 ± 8.15* |
| 0.1 | 8.72 ± 2.98* | −85.59 ± 4.92* |
| 1.0 | 18.47 ± 4.82* | −69.47 ± 7.96* |

*$P < 0.05$ in comparison with control

It can be seen that GMDP, at all the doses investigated, substantially (by an average of 4-fold) shortened the duration of hexobarbital-induced narcosis.

In the following examples, it is demonstrated that GMDP is capable of enhancing the biotransformation of various chemical substances by means of its effect on the cytochrome $P_{450}$ system.

Firstly, it was discovered that there is direct interaction of GMDP with cytochrome $P_{450}$ molecule in the microsomal fraction of the liver.

The cytochrome $P_{450}$ system is a system by means of which toxins are metabolised in the liver. A wide variety of substances combine with oxidised liver microsomal cytochrome $P_{450}$ bringing about a change in absorbency. It has been shown that various drugs, substrates and inhibitors react with microsomal cytochrome $P_{450}$ to give three characteristic types of spectral change. Subsequently, a means of estimating an apparent binding constant from these spectral data was suggested.

The three types of spectral changes are as follows.
i) For substances such as ethylmorphine or hexobarbital, the minimum difference in the spectrum occurs at about 420 nm and the maximum at about 385–390 nm. These substances are designated type I compounds).
ii) For compounds such as aniline or nicotinamide, the minimum difference in the spectrum occurs at about 390–410 nm and the maximum at about 430 nm. These substances are designated type II compounds.
iii) Some compounds are apparently type II substrates but actually act by displacing endogenous type I substrates when added to microsomes. These compounds are designated reverse type I substrates.

It has been shown that, for a number of substrates, the apparent binding constants calculated from spectral changes are related to the actual binding of type I substrates at the active site. A correlation has been demonstrated between substrate binding difference chemical data, the initial rate of the fast phase of reduction of cytochrome $P_{450}$ and hydroxylation by microsomal preparations.

We have demonstrated that there is an interaction between liver microsomal cytochrome $P_{450}$ and GMDP.

It has been demonstrated that the addition of peptide to particulate suspensions of microsomes containing cytochrome $P_{450}$ resulted in characteristic Soret spectral transition. GMDP was found to elicit a type I optical difference spectrum ($\lambda_{max}=390$ nm, $\lambda_{min}=421$ nm) in oxidised microsomes from phenobarbital-induced rat liver. $K_s$ (spectral association constant) was 0.1 mM. This is $K_s$ for the well known cytochrome $P_{450}$ HEXENAL™.

Addition of GMDP to isolated LM2 form of cytochrome $P_{450}$ in monomeric reconstituted system resulted in similar manifestation of substrate-enzyme interaction.

These investigations are of great importance for the understanding of mechanisms of action of GMDP and its analogues, not only as inducers of detoxicating oxidation processes but also for the understanding of immunological effects.

It has been discovered that GMDP, when injected into animals, induces the cytochrome $P_{450}$ system in liver microsomes and thus enhances biotransformation (oxidation) of various substances. These substances are not necessarily similar in their chemical structure; for example, benzo(a)pyrene and aniline, which are representatives of type I and type II substrates respectively for cytochrome $P_{450}$, are both metabolised more quickly in the presence of GMDP.

EXAMPLE 6

The experiments were performed on white male mice with a mass of 1–20 g. GMDP was dissolved in isotonic solution of sodium chloride and administered by means of intraperitoneal injection once a day for 3 days, with a dose of 20 mg/kg. A corresponding volume of the solvent was administered to control animals. Each group (test and control) consisted of 8 to 10 mice. Twenty-four hours after the last injection of the substances under test (test) and the solvent (control), the animals were killed, the liver was removed and its weight was determined. This was followed by the isolation of the microsomal fraction by means of differential centrifugation. The quality protein in it was determined according to the method of Lowry et al (Lowry et al, *J. Biol. Chem.*, 193, 265–275 (1951)). Bovine serum albumin was used in the construction of calibrating plot. The content of cytochrome $P_{450}$ and $B_5$ in the liver microsomal fraction was determined by spectrophotometric method with the help of a 'Hitachi-556' spectrophotometer. The rate of oxidation of aniline (p-hydroxylation) in microsomes in the presence of NADPH was determined spectrophotometrically on the basis of p-aminophenol which has formed already. The rate of oxidation of benzo(a)pyrene (BP) in liver microsomes was determined according to the intensity of fluorescence of the forming 3-oxibenzo (a) pyrene 'Baird Nova' fluorimeter. The rate of hydroxylation of aniline and BP in microsomes was expressed in nmol of metabolites/nmol of cytochrome $P_{450}$ per 1 minute, or in nmol of metabolites/mg of microsome protein per 1 minute. Statistical processing of the obtained data was performed with the use of Student's t-test.

Results

The results show that 24 hours after a 3-day administration of GMDP, considerable induction of cytochrome $P_{450}$ enzymatic activity is observed (Table 2). Oxidation (hydroxylation) of aniline and BP considerably increase (almost twofold). The induction of these activities is reliable both when calculated in nmol/mg of microsome protein/min and when calculated in nmol/mol of cyt. $P_{450}$/min. In this case the total content of cytochrome $P_{450}$ in the liver microsomal fraction increases by a small amount.

TABLE 2

Indices of activity of mice liver cytochrome P-450 system 24 hours after the termination of GMDP injections (20 mg/kg × 3 days)

| Test | Control | GMDP | % |
|---|---|---|---|
| Liver weight mg/g of the animal weight | 80.0 | 80.0 | |
| Microsomal protein mg/g | 4.5 ± 0.16 | 5.8 ± 0.31 | 129 |

TABLE 2-continued

Indices of activity of mice liver cytochrome P-450
system 24 hours after the termination of GMDP injections
(20 mg/kg × 3 days)

| Test | Control | GMDP | % |
|---|---|---|---|
| of liver weight | | | |
| Cytochrome P-450 nmol/mg of protein | 0.65 ± 0.07 | 0.87 ± 0.06 p > 0.05 | 134 |
| Aniline-hydroxylase nmol/mg of protein per 1 minute | 0.62 ± 0.08 | 1.20 ± 0.1 p < 0.05 | 194 |
| Aniline-hydroxylase nmol/nmol of cyt. P-450 per 1 minute | 0.59 ± 0.03 | 1.05 ± 0.01 p < 0.001 | 178 |
| BP-hydroxylase nmol/mg of protein per 1 minute | 0.35 ± 0.01 | 0.6 ± 0.04 p < 0.01 | 171 |
| BP-hydroxylase nmol/nmol of cyt P-450 per 1 minute | 0.40 ± 0.07 | 0.87 ± 0.09 p < 0.05 | 218 |

Note: The results of 3 tests, each performed with the use of 8–10 animals are presented.

EXAMPLE 7

Cytochrome $P_{450}$-dependent monooxygenase activity induction in accordance with pharmacological testing of HEXENAL™ narcosis duration in mice.

In addition to the experiments, which have shown GMDP ability to interact directly with cytochrome $P_{450}$ molecule as a substrate (in vitro) and to induce cytochrome $P_{450}$ system in liver microsomes (GMDP effect in vivo), experiments for testing cytochrome $P_{450}$ system according to the duration of HEXENAL™ narcosis in mice have been carried out. It is well known that HEXENAL™ is a substrate of cytochrome $P_{450}$, and the duration of its narcotic effect clearly correlates with the rate of its oxidation in the liver cytochrome $P_{450}$ system. The method of Example 6 was repeated, but instead of aniline and benzo(a)pyrene, the ability of the microsomes to metabolise HEXENAL™ was tested. The experiments performed have shown that GMDP in small doses is capable of inducing cytochrome $P_{450}$-dependent oxidation of HEXENAL™ (Tables 3 and 4).

TABLE 3

The fast detoxication effect of GMDP
The effect of GMDP on the duration of hexenal narcosis in
C57BL/6 male mice 22–24 g: 10 animals in each group; hexenal
dose - 50 mg/kg; GMDP dose - 0???

| No. | Scheme of treatment | Narcosis duration min. (M ± m) | Narcotic effect in % from control |
|---|---|---|---|
| 1 | Control 0.95% NACL per os | 55.0 ± 3.3 | 100 |
| 2 | GMDP per os 15 min before i.p injection of hexenal | 31.3 ± 4.9 (p < 0.01) | 57 |
| 3 | Control i.p injection 0.9% NaCl | 30.3 ± 2.3 | 100 |
| 4 | GMDP i.p injection simultaneously with hexenal injection | 25.7 ± 4.9 (p > 0.05) | 85 |
| 5 | GMDP i.p. injection 30 min before hexenal injection | 18.4 ± 1.5 (p < 0.001) | 61 |
| 6 | GMDP i.p. injection 60 min before hexenal injection | 30.9 ± 5.7 | 100 |
| 7 | Control | 43.0 ± 4.3 | 100 |
| 8 | i.p. injection of 0.9% NaCl GMDP i.p. injection 10 min after hexenal injection | 41.2 ± 3.3 | 95 |

TABLE 4

The effect of 3 i.p injections of GMDP (0.01 mg/kg × 3
days) on the duration of hexenal narcosis (24 hours after
GMDP injections) in C57BL/6 mice, 22–24 g,
Ig-15 animals in each group, hexenal dose 50 mg/kg.

| No | Scheme of treatment | Narcosis duration min. (M ± m) | Narcotic effect in % from control |
|---|---|---|---|
| 1 | Control (0.9% NaCl) | 48.7 ± 3.2 | 100 |
| 2 | GMDP | 21.7 ± 5.2 (p < 0.001) | 45 |

EXAMPLE 8

Over 200 patients were enrolled in a placebo-controlled trial to determine the effect of GMDP on the outcome of colorectal surgery. Many of these patients had undergone previous chemotherapy for the treatment of cancers, often over substantial periods of time, with the result that liver damage had occurred.

Figure 5:
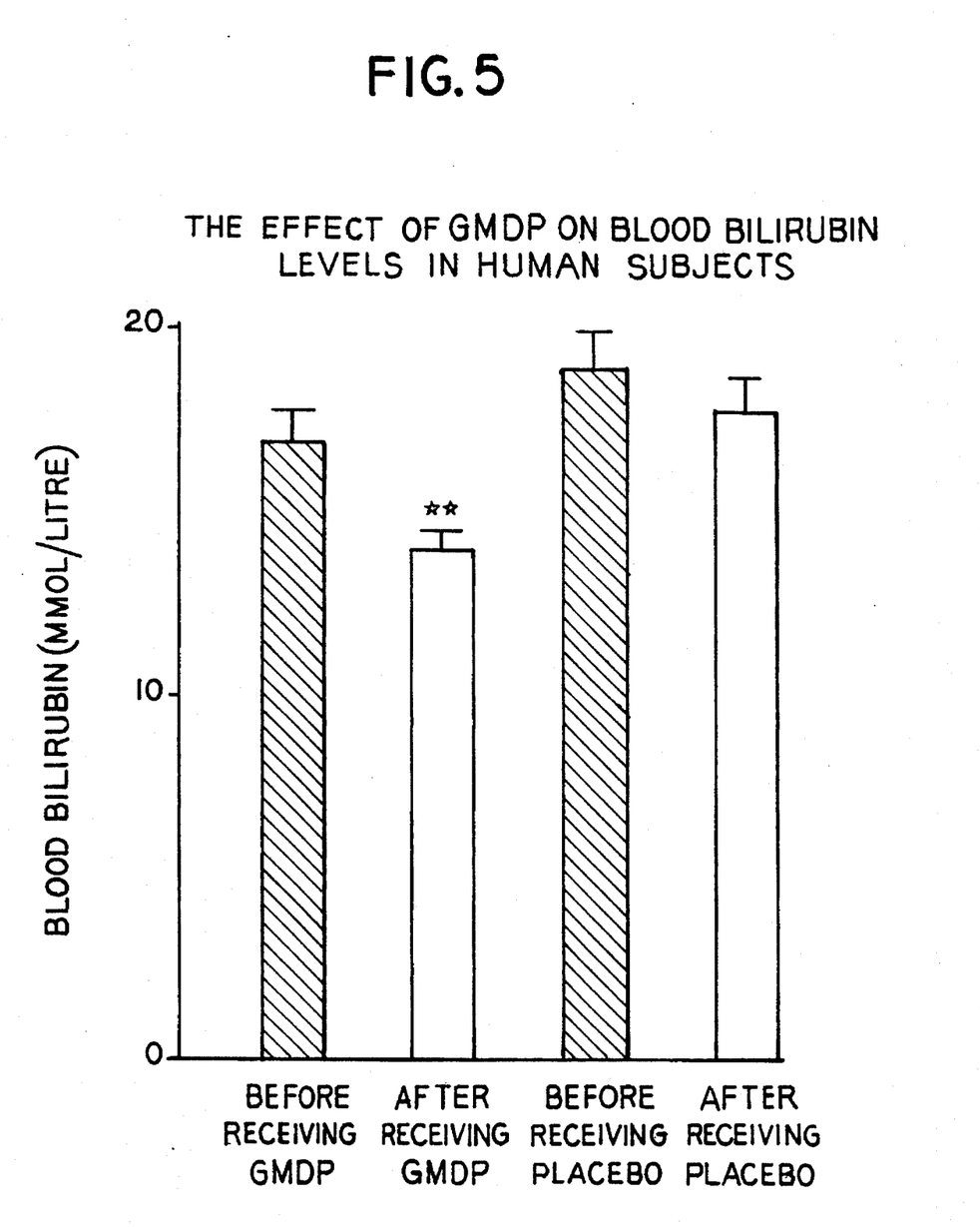
FIG. 5 shows the effect of GMDP on blood bilirubin levels in human subjects.

This was evidenced by such indicators as elevated bilirubin in their blood, resulting from the reduced ability of the liver to function as a detoxification organ. Subjects were divided into a group that received GMDP (at 1, 2 or 3 mg per day), or an inactive placebo. GMDP or placebo were administered for 10 days, and bilirubin levels in the blood were measured before and after the course of treatment. Bilirubin data were obtained from 182 of the subjects. The result is shown in FIG. 5. It is clear that the average blood level of bilirubin decreased in the GMDP-treated group and the two asterisks indicate that this decrease was statistically highly significant (p=0.002). Also, the blood level of bilirubin after GMDP treatment was significantly different from bilirubin levels after placebo treatment. Blood levels of bilirubin before the trial were not different in the two groups.

This result clearly demonstrates that GMDP treatment increases the ability of the liver to remove a metabolite from the blood.

We claim:

1. A method for detoxifying a human body containing toxins resulting from the presence of a compound taken from the group consisting of ethanol, hypnotics, anesthetics, opioids, and in vivo hepatic metabolites thereof, which comprises stimulating the activity of the cytochrome $P_{450}$ system by administering an effective amount of a muramyl peptide compound.

2. The method of claim 1 in which said compound present in a human body is ethanol.

3. A method as claimed in claim 1 wherein the muramyl peptide compound is of the formula I:

wherein:

$R^1$ represents a hydrogen atom or a $C_1$–$C_{22}$ acyl group;

$R^2$ represents a hydrogen atom or a $C_1$–$C_{22}$ acyl group;

$R^3$ represents a hydrogen atom or a $C_1$–$C_6$ alkyl group;

$R^4$ represents a $C_1$–$C_{21}$ alkyl group or a $C_6$ or $C_{10}$ aryl group;

$R^5$ represents a hydrogen atom; and

R represents the residue of an amino acid or a linear peptide built up of from 2 to 6 amino acid residues, at least one of the residues being optionally substituted with a lipophilic group.

4. A method as claimed in claim 23 wherein in the compound of general formula I:

each of $R^1$ and $R^2$ independently represents $C_1$–$C_5$ acyl group;

$R^3$ represents a $C_3$–$C_4$ alkyl group;

$R_4$ represents a $C_1$–$C_{-6}$ alkyl group;

R represents a mono-, di- or tri-peptide.

5. A method as claimed in claim 1 wherein the muramyl peptide compound is of the formula II:

wherein:

R represents a residue of an amino acid or a linear peptide built of from 2 to 6 amino acid residues, at least one of the residues being optionally substituted with a $C_{10}$–$C_{22}$ acyl or a $C_1$–$C_{10}$ ester lipophilic group; and n is 1 or 2.

6. A method as claimed in claim 5 wherein n is 1.

7. A method as claimed in claim 3 or claim 5 wherein the proximal amino acid residue is a residue of an L-amino acid.

8. A method as claimed in claim 7 wherein the proximal amino acid residue is a residue of L-alanine.

9. A method as claimed in claim 3 or claim 5 wherein the second amino acid residue from the proximal end of the peptide is of the D-configuration.

10. A method as claimed in claim 9 wherein the said second amino acid residue is of D-glutamic or D-aspartic acid or a mono-, di or mixed $C_1$–$C_{22}$ alkyl ester, an amide or $C_1$–$C_4$ alkyl amide thereof.

11. A method as claimed in claim 10 wherein the said second amino acid residue is D-isoglutaminyl or D-glutamyl.

12. A method as claimed in claim 3 or claim 5 wherein the third amino acid residue from the proximal end of the peptide is in the L-configuration.

13. A method as claimed in claim 12 wherein the third amino acid residue is L-alanyl or L-lysyl.

14. A method as claimed in claim 3 or claim 5 wherein the amino acid residue or linear peptide is substituted with at least one $C_{10}$–$C_{22}$ acyl or a $C_1$–$C_{10}$ ester lipophilic group.

15. A method as claimed in claim 3 wherein the muramyl peptide compound is:

prototype muramyl dipeptide (N-acetylmuramyl-L-alanyl-d-isoglutamine);

muroctasin, otherwise known as MDP-Lys (L18) ($N^2$-(N-acetylmuramyl-L-alanyl-D-isoglutaminyl)-$N^6$-stearoyl-L-lysine);

MTP-PE (N-acetyl-muramyl-L-alanyl-D-isoglutaminyl-L-alanyl-2-(1', 2'-dipalmitoyl-sn-glycero-3 '-hydroxyphosphoryloxy)ethylamide, monosodium);

murabutide (N-acetylmuramyl-L-alanyl-D-glutamine-α-N-butyl ester); or t-MDP (N-acetylmuramyl-L-threonyl-D-isoglutamine).

16. A method as claimed in claim 5 wherein the muramyl peptide compound is N-acetyl-glucosaminyl-N-acetyl-muramyl-L-alanyl-D-isoglutamine (GMDP).

17. A method as claimed in claim 5 wherein the muramyl peptide compound is N-acetyl-glucosaminyl-N-acetyl-muramyl-L-alanyl-D-glutamic acid (GMDP-A).

18. A method as claimed in claim 3 wherein the administration is oral.

19. A method as claimed in claim 5 wherein the administration is oral.

20. A method as claimed in claim 18 or claim 19 wherein the daily dosage is in the range of from 0.1 to 100 mg per day.

21. A method as claimed in claim 3 wherein the administration is parenteral.

22. A method as claimed in claim 5 wherein the administration is parenteral.

23. A method as claimed in claim 21 or claim 22 wherein the daily dosage is in the range of from 0.01 to 1 mg per day.

* * * * *